United States Patent [19]

Forse

[11] Patent Number: 5,403,590
[45] Date of Patent: Apr. 4, 1995

[54] METHOD OF PULSATILE DRUG INFUSION

[75] Inventor: R. Armour Forse, Brookline, Mass.

[73] Assignee: New England Deaconess Hospital Corporation, Boston, Mass.

[21] Appl. No.: 994,198

[22] Filed: Dec. 21, 1992

[51] Int. Cl.⁶ ............................................. A61K 9/08
[52] U.S. Cl. .................................... 424/422; 514/21; 514/169; 514/727
[58] Field of Search .................. 424/422; 514/727, 21, 514/169; 604/51

[56] References Cited

U.S. PATENT DOCUMENTS 5,202,323  4/1993  Tanikawa ..................... 514/236.5
5,232,705  8/1993  Wong ........................... 424/473

OTHER PUBLICATIONS

Baum, T. D. et al. (1990) J. Surg. Res. 48:629–634.
Frankel, J. P. et al. (1990) J. Neurosurg. and Psychiatry 53:96–101.
Baptista, R. J. et al. (1989) Ann. Pharmacol. 23:59–62.
Frank, W. et al. (1989) Clin. Pharmacol Ther. 46(2):234–239.
Rovers, J. P. et al. (1989) Crit. Care Med. 17(8):814–821.
Benovic, J. L. et al. (1988) Ann. Rev. Cell Biol. 4:405–428.
Miska, P. T. et al. (1988) J. Heart Transplant. 7(5):353–355.
Hola E. T. et al. (1986) Am. J. Hosp. Pharm. 43:2474–2478.
Colangello, A. et al. (1985) Am. J. Hosp. Pharm. 42:581–584.
Lefkowitz, R. J. et al. (1980) Curr. Top Cell. Regul. 127:205–230.

Primary Examiner—G. S. Kishore
Attorney, Agent, or Firm—Lahive & Cockfield

[57] ABSTRACT

A method of pulsatile infusion of a drug or other therapeutic agent is described. The pulsatile infusion method minimizes tachyphylaxis, while enabling the target cell, tissue, or organ to benefit from the administered drug or other therapeutic agent. The drug or other therapeutic agent, an agonist or antagonist for a molecule of the receptor system, is administered in a succession of at least two pulses. The pulses have a selected amplitude and duration so that the binding affinity of the receptor system molecule is decreased by a predetermined amount in response to each pulse. This predetermined amount is less than the difference between the maximum binding affinity of the receptor system molecule, when it is not exposed to either the agonist or antagonist, and its minimum binding affinity for the agonist or antagonist, when it is continuously exposed to the agonist or antagonist. The pulses are spaced apart by a selected interpulse period wherein the binding affinity of the receptor system molecule increases to the maximum value.

8 Claims, 2 Drawing Sheets

METHOD OF PULSATILE DRUG INFUSION

BACKGROUND OF THE INVENTION

The field of this invention is drug treatment, and relates particularly to the pulsed infusion of medications to treat cardiovascular disease and other cell, tissue, or organ disorders which necessitate treatment for an extended period of time. Treatment of cardiac disease may require long-term administration of drugs or other therapeutic agents to, for example, stimulate the heart muscle, keep vessels and passages clear of thrombi, or prevent organ rejection.

Current methods of drug administration for cardiac support have included the continuous infusion of a drug that is titrated to either a dose per body size or to a physiological end point, e.g., blood pressure. Both processes have been used in the administration of sympathomimetic drugs. However, it has been observed both in vivo and in vitro that with the continuous drug infusion there is tachyphylaxis to the drug, i.e., more drug is needed over time to achieve the same result. There is evidence in diverse biological systems that constant and increased doses of a specific agonist to a sympathetic receptor will result in desensitization, or the waning of the intensity of a response over time despite the continued presence of a stimulus of constant intensity (Benovic, J. L., et al., (1988) *Ann. Rev. Cell Biol.* 4:405–428; Lefkowitz, R. J., et al., (1980) *Curr. Top. Cell. Regul.* 17:205–230). Desensitization is a biochemical process that physically changes the receptor system molecule such that it is not able to respond to further administration of the therapeutic agent, thereby limiting the efficacy and duration of action. Densensitization of some receptor system molecules occurs when the molecule is phosphorylated.

Constant exposure of the receptor system molecule to the drug or other therapeutic agent may also result in down-regulation. (Lefkowitz, R. J., et al., (1980) *Curr. Top. Cell. Regul.* 17:205–230). Down-regulation occurs when there is a decrease in the number of receptor system molecules on the cell, thus decreasing the response to continued administration of the therapeutic agent.

An alternative method of drug administration known in the art is a bolus, or single, large dose of a medication administered at one time. Repeated bolus infusions of medications have been used to treat patients with terminal congestive heart failure (See, e.g., Baptista, R. J., et al., (1989) *Ann. Pharmacol.* 23:59–62) or with heart transplants (see, e.g., Miska, P. T., et al., (1988) *J. Heart Transplant*, 7(5):353–355).

However, depending on the amplitude (or magnitude) and duration of the bolus, down-regulation and/or desensitization may result. In cases where relatively high amplitude, long duration boluses are administered, there is often the same type of down-regulation and desensitization of molecules of the cell, tissue, or organ receptor system encountered with constant rate infusion of the drug or other therapeutic agent.

Thus, there is a need for an application technique that optimizes the effect of drug infusion, while minimizing the development and effects of resulting down-regulation and/or desensitization. Accordingly, it is an object of this invention to provide a method of pulsed application of a drug or other therapeutic agent that is at least as effective as a method of continuous administration. It is also an object of the invention to provide a method of drug administration which requires a lesser amount of drug or other therapeutic agent for the same response. An additional object is to provide a method of long-term administration of a drug or other therapeutic agent that minimizes the development and effects of down-regulation and/or desensitization of the target tissue to the administered agent.

SUMMARY OF THE INVENTION

This invention provides a method of pulsatile infusion of a drug or other therapeutic agent designed to overcome or limit molecular mechanisms of a cell, tissue, or organ receptor system.

A method of administration has been developed which minimizes tachyphylaxis, while enabling the target cell, tissue, or organ to receive the benefits of the administered drug or therapeutic agent and maintain its relative health.

In the preferred form of this method, a drug or other therapeutic agent is provided in a physiologically acceptable solution. It is administered in a succession of at least two pulses. The drug or other therapeutic agent is an agonist or an antagonist which is specific for a molecule of the receptor system. The agonist or antagonist is either an endogenous or exogenous ligand for the receptor system molecule. The receptor system molecule can be any cell-associated molecule to which an agonist or antagonist binds to initiate its effects.

The receptor system molecule is characterized by a binding affinity for the agonist or antagonist which decreases as a function of time toward a minimum value ($K_a$min) when the molecule is continuously exposed to the agonist or antagonist at a concentration at or above a predetermined value, and which increases as a function of time toward a maximum value ($K_a$max) when the molecule is not exposed to either the agonist or antagonist.

The pulses of the drug or other therapeutic agent each have a selected amplitude and duration so that the binding affinity of the receptor system molecule is decreased by a predetermined amount in response to each pulse. This predetermined amount is less than the difference between the $K_a$max and the $K_a$min. The pulses are spaced apart by a selected interpulse period. In response to each interpulse period, the binding affinity increases to the maximum value.

In various embodiments of the invention, the pulses administered are controlled to be substantially rectangular, although other pulse shapes may be used. Preferably, the administering step includes the substep of controlling the amplitude and duration of the pulse period and interpulse period whereby the binding affinity has a relatively high (i.e., near $K_a$max) predetermined average value ($K_a$av).

Where the disorder to be treated is a deficiency of an endogenous ligand which can bind effectively to a molecule of the receptor system, the drug or other therapeutic agent to be administered is preferably a pharmacologic agent such as isoproterenol or a physiological hormone such as insulin, cortisol, glucocorticoid, luteinizing hormone, follicle stimulating hormone, thyroid hormone, mineralocorticoid, or a catecholamine such as adrenalin or noradrenalin.

When the disorder to be treated is a cardiac disorder, one preferable therapeutic agent is a β-adrenergic receptor agonist such as isoproterenol.

BRIEF DESCRIPTION OF THE DRAWINGS

The foregoing and other objects of this invention, the various features thereof, as well as the invention itself may be more fully understood from the following description when read together with the accompanying drawings in which.

DESCRIPTION OF THE INVENTION

Figure 1:
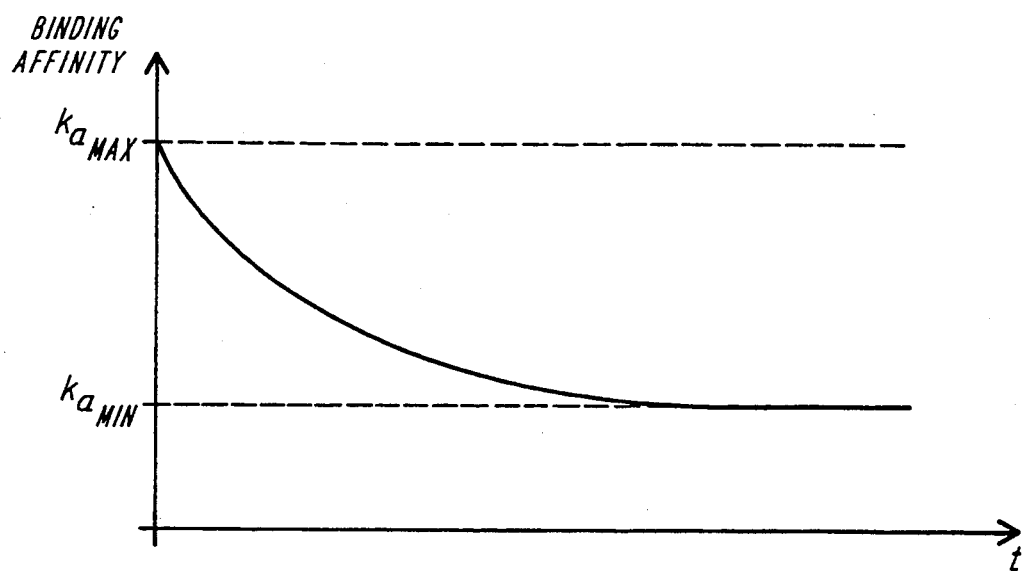
FIG. 1 is a graphic representation showing the binding affinity plotted as a function of time for beta receptors on the surface of cardiac tissue in response to the application of a step concentration change in isoproterenol from 0 to 500 μg/l at time (t)=0.

In order to avoid tachyphylaxis, the pulsatile therapeutic agent infusion method of the invention is designed either to overcome or to limit regulatory mechanisms of molecules of the receptor system.

Briefly, the method provides for the administration of periodic pulses of a drug or other therapeutic agent where the pulse amplitudes, durations, and interpulse periods are optimally selected to maximize the therapeutic effect per unit drug or agent administered. By periodically pulsing the drug or other therapeutic agent (i.e., either an agonist or antagonist for the receptor system molecule) so that the binding affinity ($K_a$) of the receptor system molecule for the agent is maintained at or near its maximum value, less total agent is needed for the same therapeutic effect, as compared with prior art drug administration techniques. A continuously-treated cell, tissue, or organ shows a decrease in its normal function after long-term treatment.

In contrast, pulsatile drug administration allows the target cell, tissue, or organ, to maintain its ability to perform its normal functions despite long-term treatment. Periodic pulsing leaves the receptor system molecule less desensitized and/or down-regulated, and thus, better able to respond to further agonist or antagonist administration. Thus, this method avoids tachyphylaxis, which usually accompanies long-term and even short-term continuous agonist administration procedures.

The pulsatile drug administration method of this invention is particularly adapted for providing therapeutic effects to patients afflicted with a disorder of a cell, tissue, or organ. The drug or other therapeutic agent is an agonist or antagonist which is specific for a molecule of the cell, tissue, or organ receptor system. The agonist or antagonist can be an endogenous or exogenous ligand for the receptor system molecule. The agonist is a molecule which binds to a molecule of the receptor system and changes the function of the receptor system molecule to which it binds. Conversely, an antagonist is a molecule which binds to a molecule of the receptor system without altering the receptor system molecule's function. The effect of an antagonist, therefore, depends upon its ability to prevent the binding of the agonist, thereby blocking the agonist's biological actions.

The receptor system molecule can be any cell-associated molecule to which an agonist or antagonist binds to initiate its effects. The binding affinity of the receptor system molecule for the ligand is dependent on the histological environment. More particularly, the binding affinity of the receptor system molecule decreases as a function of time toward a minimum value when the molecule is exposed to the ligand in concentrations at or above a predetermined value; the binding affinity increases as a function of time toward a maximum value when the molecule is not exposed to the ligand. Examples of molecules of a cell, tissue, or organ receptor system which may bind the agonist or antagonist include membrane-bound molecules having extracellular agonist or antagonist binding sites (e.g., S-adrenergic receptors, insulin receptors) and membrane-bound molecules (e.g., G proteins, adenylyl cyclase) and intracellular molecules (e.g., cytoplasmic and nuclear steroid hormone receptors, cyclic AMP) that act as signal transducers.

Figure 2:
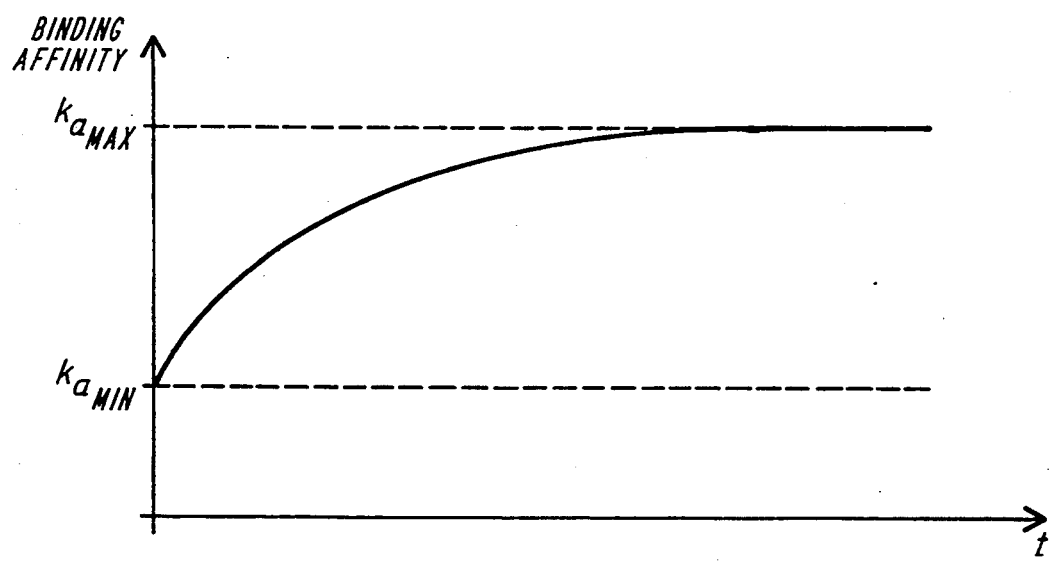
FIG. 2 is a graphic representation showing the binding affinity plotted as a function of time for the receptors described in FIG. 1 after exposure to a high concentration of ligand just prior to t=0, in response to a zero concentration after t=0.

Such a ligand-receptor system molecule relationship is illustrated in FIGS. 1 and 2. FIG. 1 shows the binding affinity plotted as a function of time for β-adrenergic receptors on the surface of cardiac tissue in response to the application of a step concentration change in isoproterenol from 0 to 500 μg/l at time (t)=0; $K_a$ decreases in a substantially exponential manner from a maximum value $K_a$max to a minimum value $K_a$min. FIG. 2 shows the binding affinity plotted as a function of time for those same receptors after exposure to a high concentration of ligand just prior to t=0; binding affinity at t=0 is at the minimum value $K_a$min), in response to a zero concentration after t=0; binding affinity increases in a substantially exponential manner from the minimum value $K_a$min to the maximum value $K_a$max.

Figure 3:
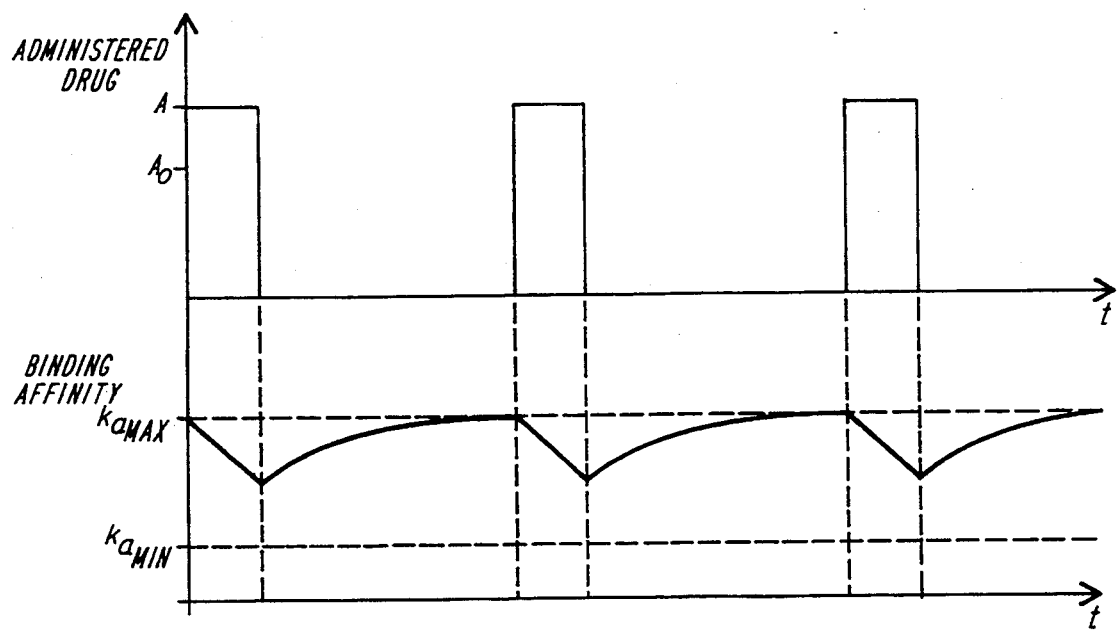
FIG. 3 is a dual plot showing both administered drug and binding affinity as a function of time on a common time axis.

To implement the invention, a succession of pulses of the ligand is either parenterally or enterally administered to the patient. FIG. 3 shows a dual plot showing both administered ligand and binding affinity as a function of time on a common time axis. As illustrated, the ligand pulses are "rectangular", having a height (or amplitude) A and a duration PW. Each pulse is separated from its predecessor by an interpulse period IPP. In other embodiments, different shaped pulses may be used. In the illustrated example of FIG. 3, the amplitude A exceeds the predetermined value $A_0$, above which the binding affinity decreases with time. During the interpulse period, essentially zero concentration of the ligand is administered. As shown in FIG. 3, the binding affinity (which starts at $K_a$max at t=0) decreases during the pulses, due to down-regulation and/or desensitization, but recovers to $K_a$max during the interpulse periods. As illustrated, PW is selected to be relatively short so that binding affinity does not fall off very much during the pulses, and IPP is selected to permit substantially full recovery of binding affinity to its maximum value before the next pulse. As a consequence, the binding affinity remains relatively high throughout the entire period of pulsatile administration.

With this relatively high binding affinity, the efficiency (per unit ligand) of ligand delivery to the target tissue or organ is correspondingly high during times of relatively high concentration, i.e., during or shortly after each pulse. In contrast, under a prior art administration technique wherein a continuously high level of ligand concentration is maintained, the resultant decrease in binding affinity over time results in a relatively low efficiency (per unit ligand) of ligand delivery. Thus, in accordance with the present invention, the pulse shape and repetition rate can be selected to provide a substantially equal or better therapeutic effect than that achieved by a constant rate of drug administration. The relatively high delivery efficiency results in an equal or better therapeutic effect with less total ligand volume.

The method of the invention can be adapted to any ligand-receptor system molecule interaction where the binding affinity may change as the result of down-regulation and/or desensitization. Such interactions include those involving endogenous ligands such as insulin, cortisol, glucocorticoids, luteinizing hormone, follicle stimulating hormone, thyroid hormones, mineralocorticoids, and catecholamines, and their receptors. These endogenous ligands may be isolated from natural sources according to methods and procedures known in the art, or in some cases, may be commercially obtained.

Alternatively, these interactions may involve a receptor system molecule and an exogenous ligand or an analog of an endogenous ligand which can bind the receptor system molecule and trigger a similar response. Examples of such interactions include a $\beta$-adrenergic receptor and the exogenous ligand isoproterenol and an $H_2$ receptor and an exogenous ligand such as cimetidine. Such exogenous ligands and analogs of endogenous ligands may be prepared by recombinant DNA techniques or may be biochemically synthesized using methods known by those skilled in the art. These drugs may be developed with varying half-lives to optimize the pulsed infusion.

Applications of the pulsatile infusion method include treatment of a variety of patients who require cardiac support by drug administration. This includes patients with heart transplants, congestive heart failure, and those with low cardiac output caused by hypovolemia or sepsis.

In addition, patients with other cell, tissue, or organ disorders such as deficiencies in, or overproduction of, various physiological hormones or substances can be treated by pulsed administration. For example, patients with Parkinson's disease, characterized by a deficiency in dopamine, may be treated with endogenous ligands such as dopamine precursors (e.g., levodopa), active analogs of endogenous ligands, or exogenous ligands; patients with ulcers resulting from the overproduction of gastric acid may be treated with cimetidine, ranitidine, famotidine, or other $H_2$-receptor exogenous ligands or drugs which suppress gastric acid production (See e.g., Rovers, J. P., et al., (1989) *Crit. Care Med.* 17(8):814–821; Frank, W., et al., (1989) *Clin. Pharmacol. Ther.* 46(2):234–239)).

The pulse of drug or other therapeutic agent may be administered intravenously, intramuscularly, or locally into or at the target tissue or organ, depending on the target to be treated. Enteral administration of the therapeutic agent is also possible. Administration may be effectuated via manual techniques including the bolus administration of a predetermined amount of drug for a predetermined amount of time at a predetermined rate. Alternatively, mechanized pumps may be used with tubing that provides accurate and consistent administration and that are able to vary a number of parameters including pulse time and shape. See Hola, E. T., et al., (1986) *Am. J. Hosp. Pharm.* 43:2474–2478 and Colangello, A., et al., (1985) *Am. J. Hosp. Pharm.* 42:581–584 for prior art examples of useful pumps.

The model system used to demonstrate this invention includes a well-described cardiac preparation. Baum, T. D., et al., (1990) *J. Surg. Res.* 48:629–634. The heart is removed from a mammalian animal such as a rat, dog, or sheep and placed in a bath perfused with a physiological medium that is aerated with oxygen. The pulse and force of the heart contraction can be measured using an isometric force transducer or by the inflated balloon method.

The transducer designed to measure heart contraction may be modified to allow a constant flow of media through the organ bath, thus enabling quick changes in the atrial environment due to the addition or removal of a drug from the bath. Another modification may include addition of a coloring agent (e.g., methylene blue) to the bath when the drug or therapeutic agent is added. This allows for an assessment of the period of time the drug is in contact with the cardiac preparation.

The invention may be more fully understood from the following examples which are not meant to limit the scope of the invention, since alternative methods may be used to obtain similar results. For example, other cardiac drugs such as sympathomimetic drugs can be provided in a pulsatile or intermittent fashion. Alternatively, drugs for other organ disorders can be administered by the pulsatile method of the invention. Of course, the timing of drug pulses will vary depending on the class of drugs and the patient's response. While it is possible that the length of the pulse could be fixed, it may also vary in clinical application, e.g., from milliseconds to minutes.

EXAMPLE 1

A. Cardiac Preparation

The experiment was carried out using the method as described by Baum, T. D., et al. (1990), *J. Surg. Res.* 48:629–634 with modifications. A 300 g Sprague-Dawley rat was sacrificed by guillotine decapitation. The thorax was opened and the whole heart was excised. The heart preparation was then placed in warm, freshly bubbled Krebs Heinselet (K-H) solution (95% $O_2$ and 5% $CO_2$) and rapidly transported to the organ bath. The atria of the heart were dissected from the cardiac preparation and then suspended in the organ bath apparatus filled with the warm K-H solution that was continuously aerated with the gas mixture at 1.5 liters/minute. The atria were then attached to the isometric force transducer (Grass FT03, Grass Instruments, Quincy, Mass.) to measure the force of contraction. A preload or tension of 0.25 g was placed on the atria which were allowed to equilibrate for 10 minutes.

B. Drug Administration

Isoproterenol, a specific $\beta$-adrenergic receptor agonist, was diluted, for both the continuous and pulsatile infusion studies, in the K-H solution to a concentration of 4 $\mu$g/l. Isoproterenol has a relatively short half-life (approximately two minutes). One run for the continuous infusion study and two runs for the pulsatile infusion studies were completed. The isoproterenol solution was infused either continuously for thirty-five minutes or in pulses with 20 seconds on and 20 seconds off for either forty or fifty minutes. Two preparations were carried out with the K-H being pumped through the organ bath at a rate of 200 ml/min. The atrial preload was set at 0.5 g. Initially, the atrial preparation was stimulated with isoproterenol for two hours and then allowed to rest. This provided for an atrial preparation that was slightly fatigued, a state in which we would be using the drug for force stimulation.

C. Results

The first run was thirty-five minutes of continuously infused isoproterenol. The initial force of contraction was 0.9 g. At the end of the period the force had dropped to 0.6 g. The atrial preparation was allowed to rest for five minutes, and returned to a baseline force of 0.3 g. The fifty minute pulsatile infusion was intentionally applied after the continuous infusion, thus placing it at a disadvantage. The initial force of contraction using pulsed isoproterenol was 1.0 g, with the force oscillating between 0.8 g and 0.7 g during the pulses. With the pulse infusion "on" the force was 0.8 g after 50 minutes. The final force of contraction of the atria subject to pulsatile drug infusion showed a decrease of 0.2 g from the initial force of contraction, 0.1 g less than that which occurred in the atria subject to continuous drug infusion. The atrial preparation was then allowed to rest for twenty minutes returning to a basal contraction force of 0.3 g.

During the second run of the pulsatile drug infusion, the initial force of contraction was 0.9 g, with oscillations between 0.8 g and 0.75 g. With the pulse infusion "on", the force was 0.75 g after forty minutes. The final force of contraction of the atria subject to pulsatile drug infusion showed a decrease of 0.15 g from the initial force of contraction, 0.15 g less than that which occurred in the atria subject to continuous drug infusion.

The results from these runs are summarized in TABLE I.

TABLE I

| Condition | Base Force (g) | Initial Force (g) | Final Force (g) | Delta Force (g) |
|---|---|---|---|---|
| continuous | 0.30 | 0.90 | 0.60 | −0.30 |
| pulse | 0.30 | 1.00 | 0.80 | −0.20 |
| pulse | 0.30 | 0.90 | 0.75 | −0.15 |

These data indicate that stimulation of the atrial preparation using the pulsatile infusion method results in a response similar to that shown using the continuous infusion method. With the pulsatile administration method, however, less drug was needed to obtain the similar effect.

In addition, the final force of contraction was less with the continuous infusion than with the pulsatile infusion. This result suggests that the atrial preparation and its receptor system molecules were in better physiological condition after the pulsed infusion than after the continuous infusion. This may be due to a better state of the receptor system molecules, as receptor desensitization will occur over a thirty to forty minute period of continuous drug administration. In addition, the myocardial energetics or calcium balance may also be improved with the pulsed infusion.

EXAMPLE 2

The same dose of isoproterenol was administered for approximately twenty minutes to the cardiac preparation described in EXAMPLE 1.

Figure 4:
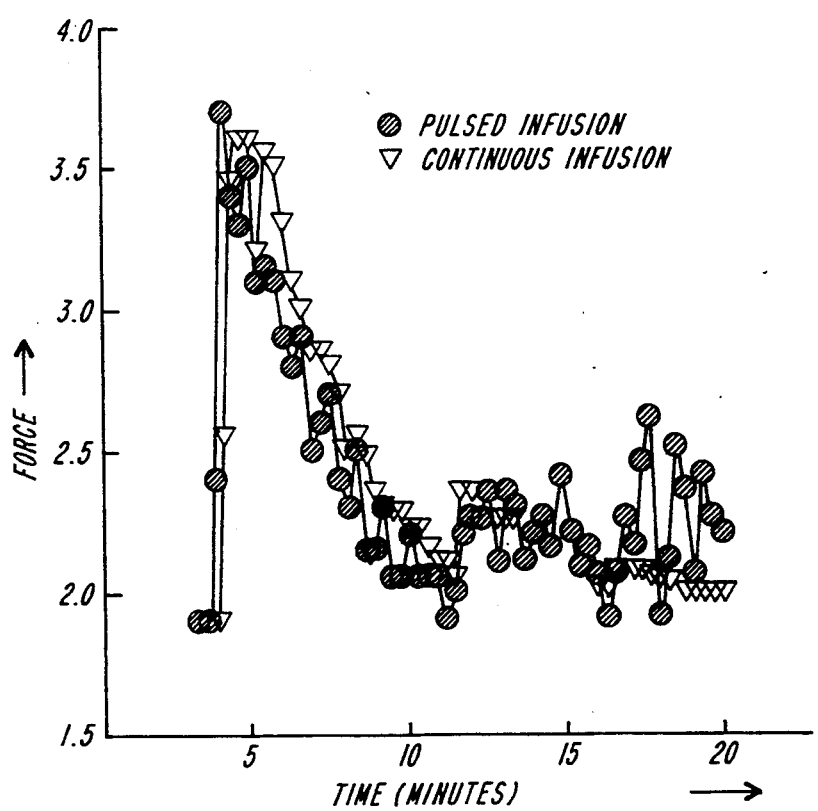
FIG. 4 is a graphic representation of the force of contraction of an in vitro cardiac preparation which was subjected to pulsatile infusion or continuous infusion of isoproterenol for varying lengths of time.

The results are presented in FIG. 4. Use of either the continuous or pulsatile infusion technique results in a period of adjustment. From the zero to the twelve minute point, the cardiac responses to the continuous and pulsatile infusions are very similar. From the twelve minute to the twenty minute point, however, the mean force of contraction of the pulsed infusion is statistically greater than that for the continuous infusion. In addition, after twenty minutes of infusion, the pulsed infusion preparation exhibits a greater force of contraction than does the continuous infusion. This second point is demonstrated in TABLE II.

TABLE II

| Time Period | Pulsed Infusion (g) | Continuous Infusion (g) | P Value |
|---|---|---|---|
| last 14 min | 2.18 ± 0.03 | 2.15 ± 0.05 | n.s. |
| last 12 min | 2.21 ± 0.03 | 2.12 ± 0.02 | p < .05 |
| last 8 min | 2.21 ± 0.04 | 2.06 ± 0.02 | p < .05 |
| last 6 min | 2.27 ± 0.06 | 2.01 ± 0.01 | p < .05 |

The mean force of contraction of preparations subject to either the pulsed or the continuous infusion is compared during four time periods. During the last twelve minutes of the infusion period, the mean force of contraction is greater with the pulsed infusion than with the continuous infusion. This difference is most apparent during the last six minutes.

Before and after the infusions described in TABLE II, the cardiac preparations were challenged with a maximal dose of isoproterenol. With the pulsed infusion, the force of contraction was 5.64 g ±0.53 before, and 5.80 g±0.73 g after, resulting in an increase of 0.16 g following the infusion period. With the continuous infusion, the force of contraction was 6.67 g±0.27 before, and 5.74 g±0.45 after, the infusion period with a resulting decrease of 0.93 g. The difference between the response before and after the infusion reflects any changes in the maximal response of the receptor system molecule to the agonist.

These data consistently demonstrate that the pulsed infusion of the $\beta$-adrenergic receptor agonist, isoproterenol, results in an improved cardiac force of contraction over time. The increased response to the isoproterenol is believed to be due to less receptor down-regulation during the pulsatile administration. With both techniques, there is improved cardiac force of contraction after one hour using the same concentration of isoproterenol. The pulsatile infusion technique, however, requires a smaller dose of isoproterenol to initiate a force of contraction similar to that produced by the continuous infusion technique. The mechanism of action of the pulsatile infusion technique probably resides in its ability to minimize down-regulation and/or desensitization of the receptor system molecules. The pulsatile method may be improved upon by using a different dose of the agonist, shorter or longer pulse periods, or an agonist with a different half-life.

The invention may be embodied in other specific forms without departing from the spirit or essential characteristics thereof. The present embodiments are, therefore, to be considered in all respects illustrative and not restrictive, the scope of the invention being indicated by the appended claims rather than by the foregoing description, and all changes which come within the meaning and range of equivalency of the claims are therefore intended to be embraced therein.

I claim:

1. A method of treating a patient afflicted with a disorder of a cell, tissue, or organ, comprising the steps of:
   (a) providing a therapeutic agent in a physiologically acceptable solution, said agent being selected from the group consisting of an agonist and an antagonist which binds a molecule of a cell or tissue receptor system, and said receptor system molecule being characterized by a binding affinity for said agent which fluctuates as a function of time between a maximum value and a minimum value in response to administration of said agent: and (b) administering a succession of at least two pulses of said agent to said patient, each of said pulses being spaced apart by a selected interpulse period, and each of said pulses having a selected amplitude and a selected duration, wherein said period, amplitude, and duration are selected such that the binding affinity of said receptor system molecule for said agent is maintained at a value which is substantially equivalent to the maximum binding affinity of said receptor system molecule for said agent.

whereby the binding of said agent to said receptor system molecule causes a response in said cell, tissue, or organ which aids in reducing said disorder.

2. The method of claim 1 wherein said administering step includes the step controlling said pulses to be substantially rectangular.

3. The method of claim 1 wherein said providing step comprises providing an agonist selected from the group consisting of an endogenous ligand and an exogenous ligand.

4. The method of claim 1 wherein said providing step comprises providing an antagonist selected from the group consisting of an endogenous ligand and an exogenous ligand.

5. The method of claim 1 wherein said disorder is a deficiency of an endogenous ligand which can bind effectively to said receptor system molecule, and said providing step comprises providing a therapeutic agent selected from the group consisting of endogenous ligands and exogenous ligands, wherein the endogenous ligands include insulin, cortisol, glucocorticoids, luteinizing hormone, follicle stimulating hormone, thyroid hormones, mineralocorticoids, and catecholamines and the exogenous ligands include isoproterenol.

6. The method of claim 5 wherein said providing step comprises providing a therapeutic agent which is a catecholamine selected from the group consisting of adrenalin and noradrenalin.

7. The method of claim 1 wherein said disorder is a cardiac disorder, and said providing step comprises providing a therapeutic agent which is a beta receptor agonist.

8. The method of claim 7 wherein, said beta receptor agonist is isoproterenol.

* * * * *